United States Patent
Roy et al.

(10) Patent No.: US 9,180,102 B2
(45) Date of Patent: Nov. 10, 2015

(54) METHODS FOR FABRICATING NANO AND MICROPARTICLES FOR DRUG DELIVERY

(75) Inventors: Krishnendu Roy, Austin, TX (US); Li Shi, Austin, TX (US); Luz Cristal S. Glangchai, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1482 days.

(21) Appl. No.: 11/418,885

(22) Filed: May 5, 2006

(65) Prior Publication Data
US 2007/0031505 A1    Feb. 8, 2007

Related U.S. Application Data

(60) Provisional application No. 60/678,639, filed on May 6, 2005, provisional application No. 60/719,844, filed on Sep. 23, 2005.

(51) Int. Cl.
| | |
|---|---|
| *A61K 9/50* | (2006.01) |
| *A61K 9/16* | (2006.01) |
| *A61K 9/51* | (2006.01) |
| *A61K 41/00* | (2006.01) |
| *B82Y 5/00* | (2011.01) |
| *B82Y 10/00* | (2011.01) |
| *B82Y 30/00* | (2011.01) |
| *B82Y 40/00* | (2011.01) |
| *G03F 7/00* | (2006.01) |

(52) U.S. Cl.
CPC ............ *A61K 9/5146* (2013.01); *A61K 41/0042* (2013.01); *B82Y 5/00* (2013.01); *B82Y 10/00* (2013.01); *B82Y 30/00* (2013.01); *B82Y 40/00* (2013.01); *G03F 7/0002* (2013.01)

(58) Field of Classification Search
CPC ... A61K 9/5146; A61K 41/0042; B82Y 5/00; B82Y 30/00; B82Y 40/00; B82Y 10/00; G03F 7/0002
See application file for complete search history.

(56) References Cited

U.S. PATENT DOCUMENTS

| | | | |
|---|---|---|---|
| 6,107,102 A | * | 8/2000 | Ferrari .......................... 436/518 |
| 6,355,270 B1 | | 3/2002 | Ferrari et al. .................. 424/489 |
| 6,873,087 B1 | * | 3/2005 | Choi et al. ............... 310/323.17 |
| 2002/0128179 A1 | | 9/2002 | Tacon et al. ...................... 514/12 |
| 2003/0114366 A1 | * | 6/2003 | Martin et al. .................... 514/12 |

FOREIGN PATENT DOCUMENTS

WO    WO 2004083902 A2 *    9/2004

OTHER PUBLICATIONS

Chou, Science, 85, 7, 1996.*
Bailey, JVSTB, 19, 2001.*
Reactive Ion Etching, Webster's Online Dictionary, 2011.*
Fite, Robotics and Automation, 1999. Proceedings. 1999 IEEE International Conference on, vol. 3, 1999.*
International Search Report and Written Opinion for application No. PCT/US2006/017312 (12 pages), Oct. 10, 2006.
N.A. Peppas et al., "Hydrogels in Pharmaceutical Formulations," European Journal of Pharmaceutics and Biopharmaceutics 50 (pp. 27-46), Jan. 28, 2000.
Lecture 16, Introduction to Optical Lithography, EECS 598-002 Winter 2006, Nanophotonics and Nano-scale Fabrication, P.C.Ku, 25 pages.

* cited by examiner

*Primary Examiner* — Susan Tran
*Assistant Examiner* — William Craigo
(74) *Attorney, Agent, or Firm* — Baker Botts L.L.P.

(57) ABSTRACT

The present invention generally relates to stimuli-responsive drug carriers and methods for making. More specifically, the present invention relates to stimuli-responsive lidded particles that respond to a physiological stimulus and dissolve at a target site inside the body thereby releasing therapeutic agents. The present invention further relates to solid, drug-loaded particles that are made from biodegradable polymers. The present invention further relates to methods for fabricating lidded particles and particles for drug delivery.

22 Claims, 9 Drawing Sheets

Figure 9:
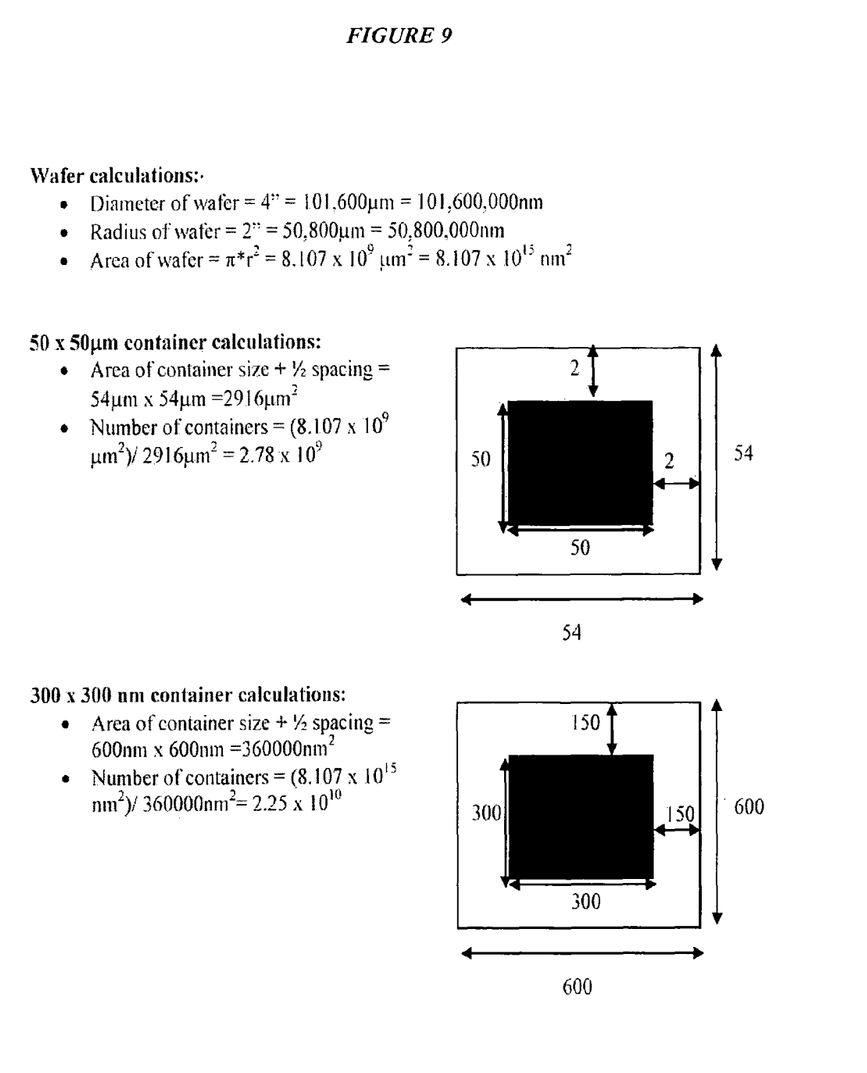
FIG. 9 is a diagram showing calculations of particle numbers from a single silicon wafer.

Wafer calculations:
- Diameter of wafer = 4" = 101,600μm = 101,600,000nm
- Radius of wafer = 2" = 50,800μm = 50,800,000nm
- Area of wafer = $\pi \ast r^2$ = 8.107 x $10^9$ μm$^2$ = 8.107 x $10^{15}$ nm$^2$

50 x 50μm container calculations:
- Area of container size + ½ spacing = 54μm x 54μm = 2916μm$^2$
- Number of containers = (8.107 x $10^9$ μm$^2$)/ 2916μm$^2$ = 2.78 x $10^9$

300 x 300 nm container calculations:
- Area of container size + ½ spacing = 600nm x 600nm = 360000nm$^2$
- Number of containers = (8.107 x $10^{15}$ nm$^2$)/ 360000nm$^2$ = 2.25 x $10^{10}$

METHODS FOR FABRICATING NANO AND MICROPARTICLES FOR DRUG DELIVERY

PRIORITY CLAIM

This application claims priority to U.S. Provisional Applications Nos. 60/678,639 filed May 6, 2005 and 60/719,844 filed Sep. 23, 2005, the contents of which are incorporated in their entireties herein.

BACKGROUND OF THE INVENTION

Therapeutic and diagnostic applications of nanofabrication technology are gaining increasing interest. Over the past several decades almost all efforts in controlled release drug delivery has been focused on polymer-based, diffusion/degradation-controlled delivery strategies. Current "controlled release" drug delivery systems are based primarily on particles or matrices of various polymers and lipids where the release of the therapeutic agent is controlled primarily by diffusion and hydrolytic degradation. Although progress has been made and several new products are coming in the market that can significantly enhance patient compliance, reduce side effects, and improve the quality of life, there remain several limitations of these approaches.

First, despite the development of sophisticated and sensitive assays to study drug release and polymer degradation in vitro, little correlation exists between in vitro observations and in vivo performance of diffusion/degradation controlled devices. The effects of tissue environments in vivo, especially tissue pH, enzymes, salt concentrations, and the rarity with which perfect sink conditions are met, makes most prediction of drug diffusion/release inherently inaccurate.

Second, delivery systems that rely on particle-based strategies, e.g., micro and nanoparticles for tissue targeted delivery, suffer from the limitation that the bottom-up synthesis processes produce a large polydisperse population of particles whose physico-chemcial characteristics, drug release profiles, degradation kinetics, and material properties become hard to evaluate and reproduce, especially at pharmaceutical scales.

Third, the lack of a stimuli-responsive release mechanism results in the release of the drug in a somewhat uncontrolled manner, which often results in systemic side effects.

Fourth, particle-based drug carriers rely on emulsion or micelle formation for synthesis and drug loading, thereby achieving only limited and often poor encapsulation efficiency. This limitation becomes particularly critical of highly expensive and difficult to synthesize drugs, leading to limited application and high cost. Strategies to enhance drug entrapment within carriers would therefore be highly beneficial.

Fifth, combining multiple functionalities (i.e., both targeting as well as stimuli-sensitive properties), in a controlled and reproducible manner is significantly difficult in self-assembled carrier systems. Polymer-based pro-drugs offer the closest design to such combinatorial approach (Ulbrich et al., *J. Control Release* 2000, 64:63-79; Peterson et al., *Adv. Exp. Med. Biol.* 2003, 519:101-23; Ulbrich et al., *J Control Release* 2003, 87:33-47; Ulbrich and Subr, *Adv. Drug Deliv. Rev.* 2004, 56:023-50; Rihova et al., *J. Control Release* 2000, 64:41-61; Kovar et al., *J. Control Release* 2004, 99:301-14; Kopecek et al., *Eur. J. Pharm. Biopharm.* 2000, 50:61-81). However, such designs do not allow for simultaneous delivery of multiple agents (drugs, contrast agents etc.) and are yet to have demonstrated conclusive clinical efficacy. Newer approaches in delivery of therapeutics are therefore urgently needed.

A key issue in drug delivery is disease-responsive release. Despite current efforts to target drug nanoparticles and liposomal drug carriers to diseased cells in vivo (Kreuter, *J. Nanosci. Nanotechnol.* 2004, 4:484-8; Park et al., *Adv. Pharmacol.* 1997, 40:399-435; Park et al., *Semin. Oncol.* 2004, 31:196-205; Noble et al., *Expert Opin. Ther. Targets* 2004, 8:335-53), it is inevitable that during transport to target cells and the extracellular residence time, significant amounts of toxic drugs will diffuse to normal tissues. A combination of both cellular targeting and disease-specific, stimuli responsive delivery would provide a significantly improved design. Although several concepts have been proposed to address the issues of stimuli responsiveness (Peppas et al., *Eur. J. Pharm. Biopharm.* 2000, 50:27-46; Miyata et al., *Adv. Drug Deliv. Rev.* 2002, 54:79-98; Qiu and Park, *Adv. Drug Deliv. Rev.* 2001, 53:321-39) and tissue targeting (Park et al., 1997, supra; Park et al., 2004, supra; Ulbrich et al., 2000, supra; Lu et al., *J. Control Release* 2002, 78:165-73), the inherent complexity of bottom-up (i.e. self-assembly) synthetic approaches (e.g., emulsions or micelles) makes it difficult to incorporate both these functionalities in a single delivery platform. A top-down nanomachining approach that would ensure triggered bolus release of drugs, primarily in response to a specific stimulus, from a highly monodisperse population of carriers could provide significantly improved alternatives to currently available diffusion/hydrolysis controlled systems.

Current MEMS-Based Drug Delivery Devices

Micro and nano-electromechanical systems have traditionally been used for the integrated circuit industry. Several groups have recently reported micro-electromechanical systems (MEMS)-based drug delivery devices (Desai et al., *Biotechnol. Bioeng.* 1998, 57:118-20; Richards Grayson et al., *Nat. Mater.* 2003, 2:767-72; Richards Grayson et al., *J. Biomed. Mater. Res. A* 2004, 69A: 502-12; Tao et al., *J. Control Release* 2003a, 88:215-28; Tao et al., *J. Biomed. Mate.r Res. A* 2003b, 67:369-75; Santini et al., *Nature* 1999, 397:335-8; Santini et al., *Angew. Chem. Int. Ed. Engl.* 2000, 39:2396-2407).

Desai et al. (1998, supra; 2001, supra) reported a micromachined nanoporous immunoisolation capsule, 4 mm×4 mm×110 µm in size, for encapsulation of islet cells and use in insulin delivery for diabetic patients. More recently, Langer and colleagues developed an implantable, controlled release microchip, 17 mm×17 mm×310 µm in size, with 34 drug reservoirs that can be used to deliver multiple drugs or doses at pre-designed time intervals (Santini et al., 1999, supra; Santini et al., 2000, supra). The reservoirs were sealed with a thin gold membrane that can be dissolved using an external electrical trigger. Subsequently the same group reported a degradable design of the multi-pulse microchip device using poly(L-lactic acid) (Richards Grayson et al., 2003, supra; Richards Grayson et al., 2004, supra). Micromachined particulate type drug delivery devices have been reported by Desai and colleagues (Tao et al., 2003a, supra; Tao et al., 2003b, supra; Ahmed et al., *J. Control Release* 2002, 81:291-306; Tao and Desai, *Adv. Drug Deliv. Rev.* 2003, 55:315-28). They developed bioadhesive microdevices fabricated either from silicon or poly(methyl methacrylate) (PMMA) for applications in oral drug delivery. The silicon devices were 50 µm with 25 µm reservoirs, and the PMMA microdevices were 150 µm with 80 µm reservoirs. Both were fabricated using standard photolithography processes. It was also shown that surface modification of the devices to attach targeting ligands (e.g., lectins) was achievable through avidin-biotin chemistry (Tao et al., 2003a, supra; Amed et al., 2002, supra).

Despite these efforts, major limitations in the drug delivery devices remain. First, these devices are too large (>50 µm) to be injected in blood. Second, they do not have any sensing mechanism to be physiologically responsive. The concept of intravenously injectable (i.e., nanosize), stimuli responsive devices of precise size and shape, capable of intracellular or intratumoral drug delivery has not been explored. For a nanofabricated device to be delivered systemically it must be at least less than 5 µm (preferably less than 1 µm) and to be efficiently internalized by non-phagocytic cells (e.g., tumor cells) it should be less than 300 nm in size. Significant technological challenges exist in fabricating such small carriers along with disease-responsive features using a purely top-down approach.

Nanoimprint Lithography

Several novel nanofabrication concepts (Colburn et al., Proc. SPIE, Mar. 15-17, 1999 3676, 379-389, 1999; Hooper et al., in 2003 Nanotechnology Conference and Trade Show—Nanotech 2003, Feb. 23-27, 2003, 3:47-50, Computational Publications, Cambridge, Mass., 2003; Johnson et al., in Proc. 28th Intl Conf. MNE, Sep. 16-19, 2002, 67-68:221-228, Elsevier, Lugano, Switzerland, 2003; Johnson et al., in Emerging Lithography Technologies VII, Feb. 25-27, 2003. 5037 1:197-202, Int. Soc. Optical Eng., Santa Clara, Calif., 2003; Resnick et al., Microelec. Eng. 2003, 69:412-419; Choi et al., in Emerging Lithographic Technologies V, Feb. 27-Mar. 1, 2001, 4343:436-442, Soc. Photo-Optical Instrumen. Eng., Santa Clara, Calif., 2001) are available, such as step-and-flash imprint lithography (S-FIL™) (Bailey et al., in Micro and Nano Engineering 2001, Sep. 16-19, 2001, 61-62:461-467, Elsevier Science B.V., Grenoble, 2002) and thermal nanoimprint lithography (ThNIL) (Chou et al., Science 1996, 272: 85-87).

S-FIL™ is essentially an improved version of a micromolding method, in which the topography of a template defines the patterns imprinted on a substrate. It is based on a very low-viscosity (approximately 2-3 cps) liquid imprinting monomer that is UV-curable. This leads to a very low pressure (<1 psi) and a room-temperature process particularly suitable for high-resolution, layer-to-layer alignment. It avoids distortion in the imprinted features, a common problem in traditional high pressure (e.g., >10 MPa)/high temperature (e.g., >glass transition temperature of the polymer film) micromolding processes. The low viscosity allows for sub-20 nm resolution and in situ, lubricated alignment corrections with sub-100 nm alignment accuracy. Further, the lubricated contact, low pressure, and room temperature minimizes template damage, and the step and repeat process allows for a small and reusable template that can handle 2-8 inch wafers.

One attractive feature of the S-FIL™ process is its ability to print three-dimensional nanostructures. The smallest line widths printed to date are 20 nm, since this is the minnimum trench width that has been fabricate on the imprint template. Smaller features such as sub-10 nm stitching errors of the electron beam lithography (EBL) tools, which were used to make the templates, have been reproduced with high fidelitiy. Three-dimensional structures can be replicated by the S-FIL™ process and patterns can be imprinted on top of existing topography by using an appropriate planarization material. The ability for 3D patterning is particularly useful for fabricating nanocontainers for drug delivery. While the nanoimprinting process is sensitive to particles and is done in a very clean environment, S-FIL™ has shown a remarkable self-cleaning capability: if a contaminated template is used to imprint, after a few imprints, a clean template and imprinted structures can be obtained.

Figure 1:
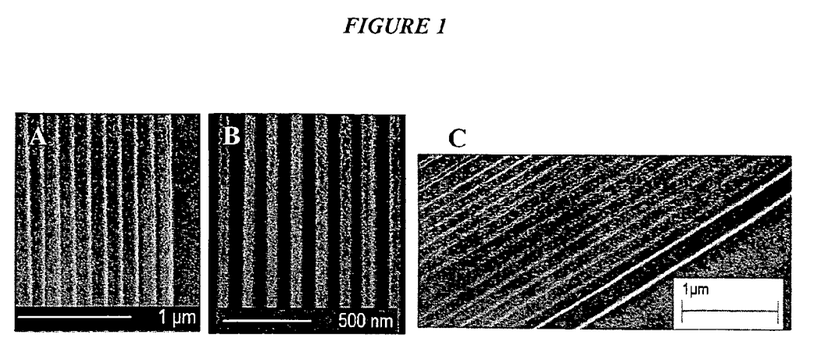
FIG. 1 is a SEM image of nano-imprint lines (3A) 20-nm-wide PMMA lines, (3B) 50-nm-wide PMMA lines, (3C) BCB lines with different line width as small as 10 nm.

A different nano-imprint process is thermal nanoimprint lithography (ThNIL) in which the device material (e.g., polymer) is heated above its glass transition temperature and imprinted using a template similar to the S-FIL™ process. The material is then cooled back to ensure a permanently imprinted topography. FIG. 1 shows scanning electron micrograph (SEM) images of PMMA and benzyclucobutene (BCB) lines patterned using a ThNIL method.

SUMMARY OF THE INVENTION

The present invention relates to stimuli-responsive drug carriers and methods for making. In a particular embodiment of the present invention, the stimuli-responsive drug carriers are nano- and microparticles with an imprinted "lid" (referred to herein as "lidded particles") that effectively "sense" a physiological stimulus (e.g., disease-specific conditions) and consequently dissolve at a target site inside the body thereby releasing therapeutic agents.

The present invention further provides for lidded particles, wherein the lidded particles are from 200 mn to 1000 nm in size. In a particular embodiment, the lidded particles of the present invention are from 200 nm to 800 nm in size. In a particular embodiment, the lidded particles are from 200 nm to 400 nm in size.

A further embodiment provides for stimuli-responsive lidded particles that can be targeted for intracellular delivery in tumor cells.

The present invention further provides for stimuli-responsive lidded particles, wherein the stimuli responded to is a disease condition. In a further embodiment, the disease condition is a tumor.

In a particular embodiment, the stimuli-responsive lidded particles are made of a biodegradable polymer such as PMMA.

The present invention further provides for lidded particles, wherein the lid is made of an enzyme-degradable, photo-crosslinkable polymer membrane. A particular embodiment provides that the enzyme-degradable lid degrades specifically in the presence of cathepsins. In a specific embodiment, the enzyme-degradable photo-crosslinkable polymer membrane of the lid is an acrylated PEG-peptide-PEG triblock copolymer membrane.

The present invention further provides drug-loaded polymer nano- and microparticles (referred to herein as "particles") that are entirely fabricated using stimuli-responsive or biodegradable polymers. The present invention further provides for drug-loaded particles, wherein the particles are from 50 mn to 1000 nm in size. In a particular embodiment, the particles of the present invention are from 50 nm to 400 nm in size. In a preferred embodiment, the particles are from 50 nm to 300 nm in size.

The invention further provides that the particles are made from biodegradable polymers, such as the biodegradable polymer PMMA. In alternative embodiments, the biodegradable polymer of the particles is PLGA.

In specific embodiments, the particles are disease-condition responsive, wherein the particle is degradable by an enzyme specifically associated or expressed in a disease state.

The present invention further provides a method for making a particle comprising providing an imprint template and a patternable biodegradable polymer; and conducting an imprint process on the polymer, thereby forming a particle. The present invention further provides for a method of making a particle, wherein the imprint template is formed using e-beam lithography, reactive ion etching, or both.

In a specific embodiment, the method for making a particle further provides that the polymer comprises a compound comprising polymethyl-methacrylate, polyethylene functionalized peptide or a combination thereof. In a particular embodiment, the method of making a particle further provides an imprint process comprising a technique comprising a thermal nanoimprint process, a S-FIL process, UV lithography or combinations thereof.

The present invention further relates to methods for making lidded particles, comprising operatively attaching a formed lid to a formed particle having a size less than about 50 nm. The invention further provides for a lidded particle formed using e-beam lithography and reactive ion etching.

In a specific embodiment, the method of making a lidded particles comprises pressing an imprint template into a UV curable monomer for S-FIL™; UV curing the monomer to form a cured monomer wafer; separating the imprint template from the cured monomer wafer; cleaning residual monomers from the cured monomer wafer; coating the cured monomer wafer with a therapeutic agent; removing excess therapeutic agent from the cured monomer wafer; pressing a second imprint template on the wafer coated with PEG-GFLGK hydrogel; UV curing the hydrogel; cleaning the cured hydrogel after the template is removed.

Both the lidded particles and particles are designed to be injected either systemically or locally for targeted delivery to diseased cells and would release the desired drug exclusively in the presence of specific physiological signals, e.g., tumor-associated enzymes.

BRIEF DESCRIPTION OF THE FIGURES

A more complete understanding of this disclosure may be acquired by referring to the following description taken in combination with the accompanying figures in which:

FIGS. 5A and 5B illustrate the EBL process for creating precise templates for nanoimprinting. FIGS. 5C and 5D show the results obtained with RIE. FIGS. 5E and 5F show the thermal imprinting process using PMMA. As shown, precise 200 nm and 400 nm particle-lid structures can be generated using this process.

DETAILED DESCRIPTION

The present invention generally relates to stimuli-responsive drug delivery particles, and methods for making such particles. The particles of the present invention comprise two types—"lidded particles" and "particles."

Lidded Particles

Figure 2:
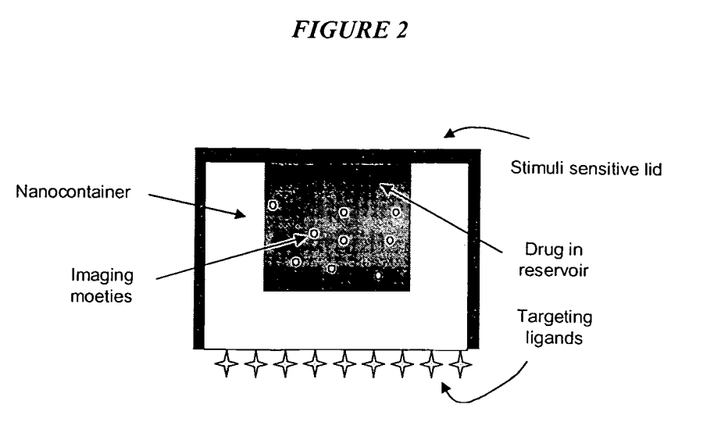
FIG. 2 is schematic diagram of a disease-responsive drug delivery nanocontainer with potential targeting and simultaneous imaging capabilities.

According to the present invention, "lidded particles" are biocompatible nano- or microparticles fabricated by nano- or microfabrication techniques that further comprise an enzymatically degradable lid that can "sense" a physiological stimulus and dissolve at a target site inside the body, thereby releasing therapeutic agents (FIG. 2).

In a specific embodiment, the present invention relates to injectable lidded particles (200-800 nm overall dimension with <50 nm features) with a nanoimprinted "lid" that can effectively "sense" a physiological stimulus (disease-specific) and consequently release therapeutic agents at a target site inside the body. In particular embodiments, the nanocontainers are on the order of 200-800 nm overall dimension with less than 50 nm features. In a specific embodiment, the lidded particles are injected systemically. In an alternate embodiment, the nanocontainers are injected locally for targeted delivery to diseased cells. In a specific embodiment, the locally targeted lidded particles would release the desired drug exclusively in the presence of specific physiological signals, e.g., tumor-associated enzymes.

In specific embodiments, the lidded particles of the present invention further comprise a payload, such as a therapeutic agent. The present invention also provides methods of making such containers. The lidded particles of the present invention may be capable of containing a payload for release at a desired time or location, or both. Accordingly, the lidded particles of the present invention may be suitable for use in a subject, for example, an animal subject (e.g., a human), and the lidded particles of the present invention may be used in methods for treating a subject.

Particles

According to the present invention, "particles" are biocompatible nano-or microparticles fabricated by nano- or microfabrication techniques. In the context of this disclosure, the term "nanoparticles," microparticles" and "particles" may be used interchangeably.

In specific embodiments, the particles of the present invention further comprise a payload, such as a therapeutic agent. The present invention also provides methods of making such particles. The particles of the present invention may be capable of containing a payload for release at a desired time. Accordingly, the particles of the present invention may be suitable for use in a subject, for example, an animal subject (e.g., a human), and the particles of the present invention may be used in methods for treating a subject.

Targeting Devices (Lidded Particles and Particles)

In certain embodiments, the devices (lidded particles and particles) of the present invention may be capable of targeting specific cells or tissues, such as diseased cells or tissues. For example, ligands and biomolecules specific for a target cells may be chemically conjugated to the device surface using standard techniques.

In some embodiments, the lidded particles and particles of the present invention may be suitable as a stimuli-responsive drug release device. The lidded particles and particles of this embodiment comprise a stimuli-sensitive release mechanism, nanofabricated into the container or particle structure. Such mechanisms may be used, among other things, to enhance delivery of a therapeutic agent by allowing release/administration of the therapeutic agent in response to a subject's therapeutic needs. In many instances, this could reduce systemic side effects, among other things, by targeting release and administration of the therapeutic agent to the target tissue and cellular compartments.

The lidded particles and particles of the present invention also may be used for simultaneous noninvasive monitoring of a therapeutic agent and the container and particle, following administration. For example, imaging contrast agents are incorporated along with the therapeutic drugs. Examples of imaging contrast agents include quantum dots, gold nanoparticles or Gadalonium-diethylenetriaminepentaacetate (Gd-DTPA) (for use in magnetic resonance imaging (MRI)) and simultaneously image the particles in the body as they deliver and/or releases the drugs. Among other things, this allows the evaluation of the efficacy of the device, for example, in reaching the target cells, intracellular uptake, and subsequent therapeutic agent release. In certain embodiments, Gadalonium may be chemically conjugated to the device surface or loaded along with a therapeutic agent. Next, in vivo transport may be monitored using MRI techniques.

The lidded particles and particles may be formed from a MEMS or NEMS-based device. In general, the lidded particles and particles of the present invention have a size suitable for a desired application. For a MEMs-based lidded particle or particle of the present invention to be injectable, it must be less than about 5 µm in size. Similarly, MEMs-based lidded particles or particles of the present invention to be taken up by a non-phagocytic cell, must be at least less than 500 nm in size. Accordingly, micro-sized lidded particles and particles may be formed having a size in the range of about 0.5 µm to about 50 µm. Nano-sized lidded particles and particles may be formed having sizes less than about 500 nm, among other things, for applications in which injection into a subject is desired.

The lidded particles and particles of the present invention may be formed using any suitable fabrication technique. For example, lidded particles and particles may be formed using nano-imprint lithography techniques. In some embodiments, the present invention uses a top-down micro- or nanofabrication technology coupled with an enzymatically degradable polymer to form injectable micro- and nanocontainers (the lidded particles). In specific embodiments, particles and lidded particles may be formed using s-FIL techniques. These fabrication techniques, among other things, may allow for exquisite control over the size and shape of the particles and lidded particles and would produce highly monodisperse population of particles. This may allow precise control of drug release kinetics and tissue targeting with little or no batch-to-batch variation in properties.

The lidded particles and particles of the present invention may be formed from any biocompatible material, for example, PMMA, silicon and silicon derivatives. In some embodiments, the lidded particles and particles may be formed of a biodegradable material, for example, a biodegradable polymer. Biodegradable polymers include, without limitation, poly(D,L-lactide-co-glycolide) (PLGA), polylactic acid (PLA), polyglycolic acid (PGA), polycaprolactone (PCL), or polyethylene glycol (PEG). Accordingly, the lidded particles and particles may be a MEMS or NEMS type device that is either silicon-based, polymer-based or both.

Polymer-based MEMS or NEMS may be formed using patternable polymers with a number of different lithography methods, such as resists for photolithography (e.g., the AZ5209 photoresist), the organosilicon monomer for S-FIL (e.g., UV photopolymerizable polymer such as PEGDMA), and polymethylmethacrylate (PMMA) that can be used for nano-imprint or electron beam lithography, or such polymers as poly(D,L-lactide-co-glycolide) (PLGA), polylactic acid (PLA), polyglycolic acid (PGA), polycaprolactone (PCL), or polyethylene glycol (PEG). A wide variety of patternable polymers are available, and the particular patternable polymer chosen may depend on the particular application (e.g., delivery of a therapeutic agent) or desired properties of the lidded particles and particles (e.g., biocompatibility, biodegradability, or mechanical robustness).

Stimuli-Sensitive Hydrogels

In particular embodiments, the lidded particles and particles may be comprised of a material that provides for stimuli-sensitive release mechanism. This would reduce systemic side effects and target the payload only to diseased tissues and specific cellular compartments. Stimuli sensitive hydrogels have been developed as 'smart' drug delivery systems and biomimetic tissue engineering scaffolds to sense environmental changes and induce a structural change or degradation (Lutolf et al., *Proc. Natl. Acad. Sci. USA* 2003, 100:5413-8; Mann et al., *Biomaterials* 2001, 22:3045-51; Peppas et al., *Eur. J. Pharm. Biopharm.* 2000, 50:27-46; Miyata et al., *Adv. Drug Deliv. Rev.* 2002, 54:79-98; Qiu and Park, *Adv. Drug Deliv. Rev.* 2001, 53:321-39; Seliktar et al., *J. Biomed. Mater. Res. A* 2004, 68:704-16; Urech et al., *Biomaterials* 2005, 26:1369-79; Gobin and West, FASEB J. 2002, 16:751-3. When coupled with a microfabricated reservoir, these hydrogels act as a valve, allowing highly controlled release of drugs and other molecules (Eddington and Beebe, *Adv. Drug Deliv. Rev.* 2004, 56:199-210.

Stimuli-sensitive hydrogels may be capable of sensing environmental change, which may result in a structural change. Environmentally sensitive hydrogels have many applications in drug delivery. For example, temperature and pH sensitive hydrogels can be used for site specific delivery. They utilize a change of pH or temperature in the body to trigger release of a drug. Alternately, environmentally sensitive hydrogels may respond to a biomolecule (e.g., glucose and antigens), light, magnetic fields, and ultrasound.

Stimuli-sensitive hydrogels may further include an enzyme-specific release mechanism. Such a mechanism would allow drug release within the endo-lysosomal pathway of the target cells, among other things, because enzymatic cleavage can break down polymers faster than hydrolysis. More particularly, an enzyme degradable membrane fabricated from photocrosslinked polymers may be used that should degrade when exposed to lysosomal enzymes, thus allowing, for example, the release a payload into the cell milieu, while preventing non-specific release of the payload outside target cells. An example of such an enzyme-specific release mechanism is a photocrosslinked, acrylated PEG-peptide-PEG tri-block copolymer membrane.

Lids

As used herein, "lids" of the lidded particles of the present invention operate to open the drug delivery devices in such a manner as to be stimuli-responsive. In general, the specific lid chosen may depend on the payload of the device. Thus, in certain embodiments, the lid may be chosen so as to slow or prevent the diffusion of the payload through the lid. In certain embodiments, the lid may take the form of a membrane, such as a polymer membrane. Lids may comprise a stimuli-sensitive polymer membrane. Such lids, among other things, would allow for protection of any contents or payload that may be provided by the particle. For example, such lids may be used to delay release of a therapeutic agent until a target site is reached. In this way, the lidded container may be capable of decreasing the side effects of highly toxic therapeutic agents by preventing release of them until the lidded particle reaches the cell interior and interacts with the appropriate enzymes.

In specific embodiments, the lids comprise a stimuli-sensitive hydrogel, discussed supra. When coupled with a biocompatible particle, these hydrogels can act as a type of valve (Low, *Sensors Actuators* B 2000, 67:49-160), allowing the controlled release of a payload, for example, a therapeutic agent.

In certain embodiments, the lids include an enzyme-specific release mechanism. Such a mechanism would allow drug release within the endo-lysosomal pathway of the target cells, among other things, because enzymatic cleavage can break down polymers faster than hydrolysis. More particularly, an enzyme degradable membrane fabricated from photocrosslinked polymers may be used that should degrade when exposed to lysosomal enzymes, thus allowing, for example, the release a payload into the cell milieu, while preventing non-specific release of the payload outside target cells. An example of such an enzyme-specific release mechanism is a photocrosslinked, acrylated PEG-peptide-PEG tri-block copolymer membrane.

One design criterion of the polymer and polymer membrane lids is that they should allow drug release upon enzymatic degradation and that there should be minimal diffusion of drugs through the membrane before the microcontainers have reached their targets. Hence, the crosslinking density of the membrane must be such that the pore sizes are smaller than the drug molecule sizes.

Peptide Spacer

In general, a peptide linking two polymers (termed herein a "peptide spacer") should be enzymatically degradable. Any degradable peptide that can be incorporated into a biodegradable polymer can be used. In particular embodiments, the peptide Gly-Phe-Leu-Gly (GFLG) is the enzymatically degradable peptide component of the polymer membrane lid. GFLG is a tetra-peptide sequence that has been widely used in tumor targeted polymer-drug conjugates (Peterson et al., *Adv. Exp. Med. Biol.* 2003, 519:101-23; Ulbrich et al., *J. Control Release* 2003, 87: 33-47; Kopecek et al., *Eur. J. Pharm. Biopharm.* 2000, 50:61-81). This peptide spacer is designed to degrade in the lysosome in the presence of lysosomal proteases (e.g., cathepsins). Such particle sequences have been shown to degrade in rat tritosomes and specifically by cathepsins C, H, L, and B.

Peptide spacers have been shown to have different degradation rates based on their size and amino acid sequence (Ulbrich et al., 2003, supra; Kopecek et al., 2000, supra; Etrych et al., *J. Control Release* 2001, 73:89-102). It was found that the sequence GFLG was especially sensitive to Cathepsin B, a protease that has been shown to be overexpressed in tumor cells. Specifically, Cathepsin B levels in tumor cells and tissues of patients with lung cancer, especially non-small cell lung cancer (NSCLC), is significantly elevated and has been directly related to their prognosis (Krepela et al., *Neoplasma* 1990, 37:61-70; Krepela et al., *Int. J. Cancer* 1995, 61:44-53; Krepela et al., *Neoplasma* 1997, 44:219-39; Spiess et al., *J. Histochem. Cytochem.* 1994, 42:917-29; Werle et al., *Cancer* 2000, 89:2282-91; Jessup, *Am. J. Pathol.* 1994, 145:253-62; Heidtmann et al., *Clin. Exp. Metastasis* 1997, 15:368-81; Higashiyama et al., *J. Clin. Pathol.* 1993, 46:18-22; Erdel et al., *J. Histochem. Cytochem.* 1990, 38: 1313-21; Ebert et al., *Anticancer Res.* 1994, 14: 895-9).

To facilitate a better understanding of the present invention, the following examples of specific embodiments are given. In no way should the following examples be read to limit or define the entire scope of the invention.

EXAMPLES

Example 1

Incorporation of the Peptide GFLGK in a Photocrosslinkable PEG Polymer

Figure 3:
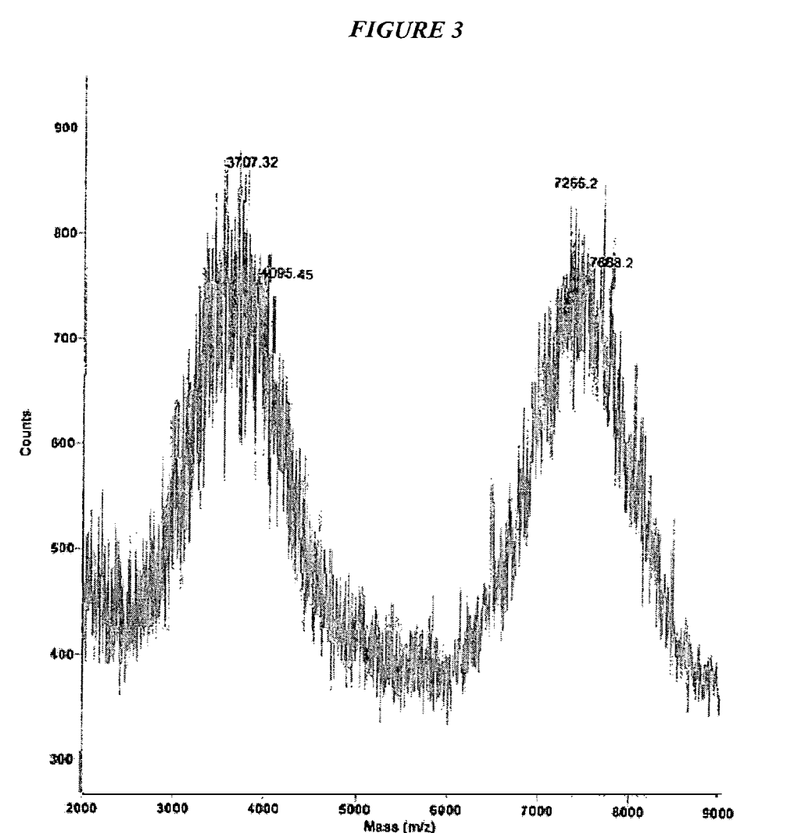
FIG. 3 is a graph showing a MALDI-TOF mass spectrometry analysis of peptide conjugation to PEG-acrylate molecules. Peaks are at 3707 and 7256 m/z.

The peptide sequence GFLGK (molecular weight (MW) 527 Daltons, synthesized at ICMB Protein Facility at the University of Texas at Austin) was reacted with acrylate-PEG-N-Hydroxy-succinamide (ACRL-PEG-NHS, MW 3,400, Nektar Therapeutics, AL). The primary (alpha) amine of Glycine (G) and the primary amine of Lysine (K) at either end of a peptide molecule reacts with the N-Hydroxy-succinamide (NHS) groups of two hetero-bifunctional PEG chains, i.e., each peptide molecule crosslinks two PEG molecules. This creates a 2:1 molar reaction (ACRL-PEG-NHS: GFLGK) to form ACRL-PEG-GFLGK-PEG-ACRL (a homobifunctional PEG diacrylate). Specifically, the peptide was dissolved to a final concentration of 1 mg/mL in 50 mM sodium bicarbonate buffer, pH 8.2. Separately, the ACRL-PEG-NHS was also dissolved in 50 mM sodium bicarbonate buffer, pH 8.2. The PEG solution (300 µL) was then added one drop at a time into the peptide solution and reacted at room temperature for 2 hours. Next the unconjugated ACRL-PEG-NHS and free peptides were removed by dialysis (Spectrum Spectra/Por 5,000 MWCO dialysis tubing, Fischer Scientific) in deionized water. The solution was dialyzed for 4 hours at room temperature and then overnight at 4° C. with periodic changing of buffer followed by lyophilization of the sample. Matrix-assisted laser desorption/ionization time-of-flight (MALDI-TOF) mass spectrometry (Perspectives Biosystems Voyager) was used to verify conjugation and removal of unconjugated material. As shown in FIG. 3 (measured before dialyzing through the 500 kD membrane), the presence of an approximately 7,000 kD peak indicates successful conjugation of one peptide to two PEG molecules. The other peaks indicate free peptide and free PEGs.

Verification of Conjugation

MALDI-TOF mass spectrometry was used to verify conjugation and removal of unconjugated material. This was performed by measuring and comparing the molecular weight distribution (MWD) of the peptide alone, ACRL-PEG-NHS (approximate MW 3,400 Daltons), and conjugated ACRL-PEG-GFLGK-PEG-ACRL approximate MW 7,000 Daltons). Dialysis through a 5,000 kD membrane yielded a nearly pure population of peptide-linked bifunctional PEG-acrylates suitable for further photocrosslinking.

Photopolymerization of ACRL-PEG-Peptide-PEG-ACRL Polymer

The photopolymerization process used is similar to that described in Hern & Hubell, *J. Biomed. Mater. Res.* 1998, 39:266-76, and Bryant et al., *Biotechnol. Bioeng.* 2004, 86:747-55, the relevant disclosures of which are incorporated herein by reference. The lyophilized ACRY-PEG-GFLGK-PEG-ACRL was dissolved in PBS in various weight percentages (20%, 30%, 50%, and 100% w/v solutions). The ultraviolet (UV) photoinitiator, 2-hydroxy-1-[4-(hydroxyethoxy) phenyl]-2-methyl-1 propanone (I2959, Ciba Geigy), was added to the polymer solution at 0.05 or 0.1 wt %. A thin square film of the hydrogel was formed by pipetting the solution onto a Teflon coated glass plate. Next, a coverslip (No. 1, Fisher) was placed over the solution, and the solution was polymerized for varying amounts of time with a UV lamp (365 nm, intensity approximately 4 mW/cm$^2$, Blak-Ray Lamp, Ted Pella Inc.).

Characterization of PEG-Peptide-PEG Membranes

One design criterion of the polymer and polymer membrane lids is that they should allow drug release upon enzymatic degradation and that there should be minimal diffusion of drugs through the membrane before the microcontainers have reached their targets. Hence, the crosslinking density of the membrane must be such that the pore sizes are smaller than the drug molecule sizes. To estimate the pore size of the crosslinked peptide-PEG membranes, hydrogel swelling studies were performed and the Peppas-Merrill equation (Peppas et al., *Eur. J. Pharm. Biopharm.*, 50, 27-46, 2000) was used to estimate molecular weight between crosslinks as well as the pore-size of the swollen membranes. This provided a basic idea on what crosslinking densities must be used to fabricate membranes for a particular drug size and provided the theoretical limitation of stimuli-responsive release from such a lid design.

Degradation of the Polymer Membrane in Presence of Relevant Enzymes

As a proof of concept, the enzyme-specific release kinetics of encapsulated plasmid DNA from a PEG-GFLGK-PEG hydrogel (100% w/v) was evaluated in vitro. The experiment was performed in duplicate in 0.01M PBS solution (pH 7.4) with 0.18% plasmid DNA (w/w of polymer). The DNA loaded hydrogels were placed in 2 mL tubes in PBS buffer (1 mL), and were placed on a shaker in an incubator at 37° C. for the duration of the study. At various time intervals (2 hrs, 4 hrs, 6 hrs, 8 hrs, 12 hrs, 24 hrs, 48 hrs, 72 hrs), buffer samples were collected. At each time point 100 µL of buffer was removed and 100 µL of fresh buffer was replaced. At the 72 hr time point, the entire PBS buffer solution was removed from the samples. Then a 1 mL solution of Cathepsin B (10 U/mL in PBS pH 5) was added to each sample. The samples were returned to the incubator and at various time intervals buffer samples were collected. Each time 100 µL of enzyme solution was removed, and 100 µL of fresh enzyme solution was replaced. The amount of plasmid DNA released into buffer was measured for each time point using the NanoDrop. As expected, when Cathepsin B was introduced, DNA was rapidly released, demonstrating that specific enzyme-induced burst release does occur (data not shown).

Another assay for the degradation of the polymer membrane utilizes rhodamine alone or various molecular weights of dextran-rhodamine conjugates (MW 10,000, 40,000, and 70,000 Daltons). Rhodamine or dextran-rhodamine mimics a small molecule drug or peptide/protein drugs and permits evaluating their diffusion through polymer membranes of various crosslink density (e.g., 10%, 50%, 75% and 100% w/w PEG-peptide-PEG polymers). To determine the rate of release of the model drug due to enzymatic degradation, degradation/release assays are performed on the polymer membranes with encapsulated model drugs (rhodamine or dextran rhodamine). Either rhodamine alone or dextran-rhodamine conjugates (Molecular Probes Inc., Eugene, Oreg.) is added to the polymer precursor prior to photopolymerization. Thin layer membranes are fabricated by spin coating the polymer solutions and photopolymerizing using a UV lamp. These rhodamine-containing polymer membranes are incubated at 37° C. either in PBS alone or in PBS containing various concentrations of Cathepsin B (e.g., 0.5 to 1 µM). These concentrations have been previously shown to be optimal for degradation of the GFLG peptide. Enzymatic degradations with Cathepsin B are performed in a series of pH conditions (e.g., pH 5, 5.5, 6, 6.5, and 7, sodium phosphate buffers) to evaluate the effects of environmental pH on enzyme activity and mimic the endolysosomal pH conditions. At various time points, rhodamine release from various membrane samples (e.g., 10-100% w/w polymer membranes) is evaluated using a fluorometer (570 nm excitation, 590-600 nm emission). Membrane crosslinking densities that allow for minimal drug release in the absence of any enzymes but allow immediate release in the presence of the enzyme are used for further studies.

Example 2

Fabrication Using Nanoimprint Lithography Technique

We employed the S-FIL nanoprint process (discussed supra) to imprint nanopatterns on polymers. In addition to the S-FIL method, we employed a thermal nanoprint process to imprint nanopatterns on a variety of other polymers including PMMA, BCB, hydrogensilsesquioxane (HSQ) and the electron beam resist ZEP 520A (FIG. 1). In this thermal nanoimprint process, the polymer film was heated to a temperature slightly higher than the glass transition temperature. The imprint template was treated with a release layer (such as Hexadecanethiol or Octanethiol for a GaAs imprint template) to facilitate the separation of the template from the polymer layer upon cooling. Because the polymer does not need to be photolinkable, the thermal nanoimprint process can be used to pattern a wide variety of polymers.

Example 3

Figure 4:
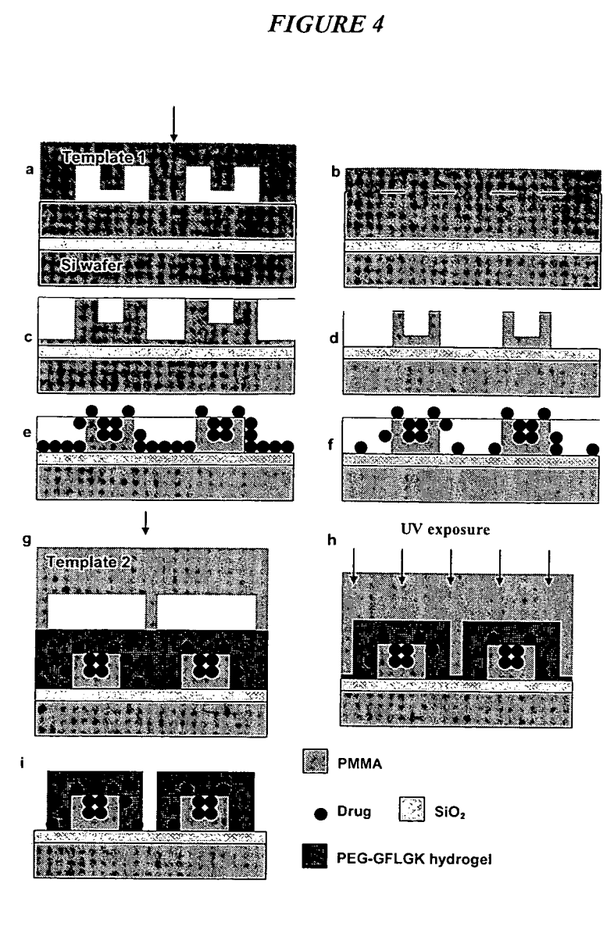
FIG. 4 is a schematic of the thermal and S-FIL™-based nanoimprint fabrication process of PMMA lidded particles with PEG-peptide-PEG lids: (4A) press an imprint template into the UV curable monomer for S-FIL™; (4B) UV curing the monomer; (4C) after the template is separated from the wafer; (4D) after a timed $O_2$ plasma cleaning of monomer residuals; (4E) spin on a therapeutic agent solution and dry; (4F) rinse and remove therapeutic agent particles from the $SiO_2$ surface; (4G) press the second imprint template on the wafer coated with PEG-GFLGK hydrogel; (4H) UV curing of the hydrogel; (4I) after the template is removed and a short $O_2$ plasma cleaning. The diagram also indicates a process involved for drug loading.
Figure 5:
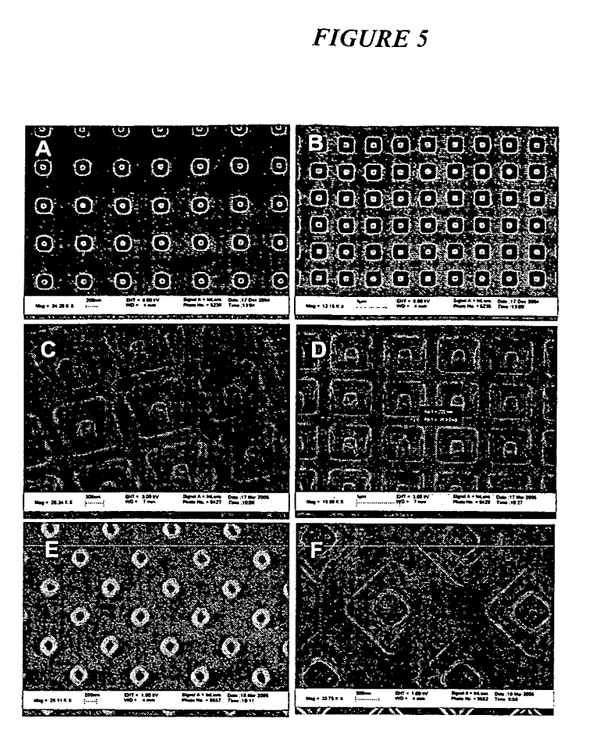
FIG. 5 is a SEM image of 200 nm (5A, 5E), 400 nm (5B, 5F, 5C) and 800 nm (5D) particles features fabricated using the proposed EBL, RIE and ThNIL techniques.

Fabrication of Templates for Thermal Nanoimprinting of Drug Delivery Lidded Particles FIG. 4 shows a schematic for the nanoimprint fabrication process of lidded particles as shown in FIG. 5, infra. Two reusable quartz templates for nanoimprinting are fabricated as described.

To make an example particle for use as a monodisperse drug carrier, we fabricated both silicon and quartz imprint templates using electron-beam lithography (EBL) combined with reactive ion etching (RIE) following an established procedure (Bailey et al., 2002, supra). Four inch p-type <100> silicon test wafers were pre-cleaned with Pirhana. The wafers were then pre-baked (180° C., 30 s), spin coated with ZEP520 (3000 rpm for 60 sec.), and finally soft-baked (180° C., 30 sec.). Next the wafers were patterned using e-beam lithography (JEOL JBX-6000FS/E) with the following process parameters: EOS mode 7, 50 kV, 100 pA, exposure level/dose: 20 to −20. Between each step the wafers were developed with ZED n50 (15-30 sec.), rinsed with isopropyl alcohol (IPA) (30 sec.), and dry etched using a Plasma Therm 790 Series Reactive ion etcher (gases: HBr, $Cl_2$, He) to etch the silicon surface below. FIG. 5 shows SEM images of device features fabricated with the EBL, REI and ThNIL techniques. FIGS. 5A-5D show a silicon wafer with an open box (lid-free particle) template for subsequent nanoimprinting. Precise template structures with sub-200 nm features can be created using this process. FIGS. 5A and 5B are SEM images of E-beam templates prior to the RIE step; 5C and 5D shows the template features following RIE.

Depending on the polymeric material used, both the thermal nanoimprint process and S-FIL process can be to make drug delivery particles. The thermal nanoimprint process was performed on a polymethyl-methacrylate (PMMA) layer (300 nm thick, 950 kD in anisole) spun on a 4-inch silicon substrate (FIG. 5E, 5F). Prior to imprinting, the imprint template was treated with a self-assembled monolayer (SAM) of Dow-corning release agent 20 to facilitate the separation of the template from the PMMA layer. The PMMA film was then heated above its glass transition temperature (105° C.) using a heater chuck under the wafer and the imprint template was pressed into the PMMA for 10 minutes using a micromanipulator with a built-in force sensor. Experiments were conducted to determine the appropriate pressure for an imprint depth of about 200 nm. The template was then lifted using the micromanipulator and separated from the wafer after the wafer temperature had reduced to 60° C. Finally, residual PMMA was removed using timed oxygen plasma cleaning and the PMMA nano-devices were released in water. These PMMA nano-boxes were released in water. As shown in the SEM images (FIG. 5E, 5F), highly precise, uniformly distributed, 200-nm and 400-nm lidded particles were fabricated using this process.

We have also employed the S-FIL™ method using an IMPRIO100 S-FIL™ tool to directly imprint peptide-functionalized PEG membranes onto a silicon substrate. The step and flash process allowed for high-throughput, wafer-scale patterning of the photolinkable polymer into drug delivery vehicles. To show that the peptide functionalized polymer membranes could be photopolymerized and imprinted using S-FIL™, we imprinted the polymer using a standard template with nano-line array patterns. We imprinted 50-nm wide nano-lines in PEG. The minimum line width that can be obtained by S-FIL™ process is smaller than 20 nm (data not shown).

Example 4

Fabrication of Lidded Particles with Stimuli-Responsive Lids Nanoimprinting of Drug-Containing Lidded Particles A schematic for the nanoimprint fabrication process of lidded particles is shown in FIG. 4. Two reusable quartz templates for nanoimprinting are fabricated as described in Example 3.

The first imprint process was performed on a PMMA layer (100 nm thick, 120 Kd molecular weight) spun on a 4 inch silicon substrate using the thermal nanoimprint setup (FIG. 4A-4C). Prior to imprinting, the imprint template was treated with a self-assembled monolayer (SAM) of Dow-Corning release agent 20, and the release layer facilitated the separation of the template from the PMMA layer. Residual PMMA (FIG. 4D) was removed using timed oxygen plasma cleaning. A therapeutic agent (e.g., drug) solution was then spin-coated on the wafer (FIG. 4E). After the solution dried, the wafer was washed briefly in DI water to remove excess drug from the $SiO_2$ surface, the side walls and the top of the PMMA lid-free particles (FIG. 4F).

To form the lid, a 100-nm thick PEG-peptide-PEG polymer (e.g., PEG-GFLK-PEG or PEG-GFLGK-PEG) layer was then coated on the wafer, and the S-FIL™ technique was used to pattern the second imprint. The second imprint template loaded in the S-FIL™ tool was pressed into the hydrogel after alignment between the alignment marks on the template and those left in the PMMA layer after the first imprint step (FIG. 4G). The UV-crosslinkable polymer was then exposed to UV light and cured (FIG. 4H). The imprint force and time was optimized, and was in the range of 2-3 N and 1-2 minute, respectively. After the template was lifted by the S-FIL™ tool and separated from the wafer, short oxygen plasma cleaning was used to clean the residual polymer and separate the nano drug containers (FIG. 4I). The size of the lidded particle was limited by the alignment accuracy between the first and second imprinting steps. Because the S-FIL™ imprint equipment can achieve sub-100 nm alignment accuracy with a minimum line width smaller than 20 nm, lidded particles of sizes 800, 500, 300, and 200 nm could be successfully fabricated.

The lidded particles are also formed using alternatives to nanoimprint lithography, such as using a combination of UV and nanoimprint lithography, as described in the following references, the relevant disclosure of each is incorporated herein by reference: Plachetka et al., *Microelectr. Eng.* 2004, 71:277-82; Forsen et al., *Microelectr. Eng.* 2002, 73-74:491-95; and Cheng and Guo, *Microelectr. Eng.* 2004, 71:288-93.

Release and Isolation of Lidded Particles

The fabricated lidded particles are released (as particles) from the wafer in a manner similar to that described by Desai and colleagues for microdevices; however, we modify that procedure to avoid high temperature or harsh chemical reactions that could potentially damage the PEG-peptide lid or the drug inside the particle. The following three methods are used evaluated to release the containers: (i) the 100 nm layer of $SiO_2$ underneath the photoresist is wet etched with a HF solution diluted in deionized (DI) water (1 part HF: 100 parts DI water) for an experimentally determined amount of time; (ii) use of a diluted base solution (6 M KOH, 5 min, 65° C.) to undercut the containers (Tao et al., *J. Control Release* 88, 215-28, 2003a; Tao et al., *J. Biomed. Mater. Res. A* 67, 369-75, 2003b); (iii) we have also found that the nano-imprinted polymer particles in FIG. 5 can be released from the wafer surface after the wafer was soaked in DI water for a long time because of the poor adhesion between the polymer and the $SiO_2$ surface. The obtained solution will be vacuum filtered through a Whatman membrane filter (0.1μ pore size, Whatman Inc., NJ) to isolate the lidded particles. The collected devices are washed and resuspended in DI water and subsequently vacuum filtered to isolate clean lidded particles. Loading levels of the protein or DNA drug are evaluated using HPLC following complete dissolution of the membrane in the presence of Cathepsin B.

Evaluation of Drug Release from Lidded Particles

To determine the enzyme-triggered drug release from the nanofabricated lidded particles, in vitro release studies are carried out in the presence or absence of Cathepsin B and an irrelevant enzyme (e.g., lysozyme) as controls. Briefly, particles loaded with the model drugs (at 1 mg/ml BSA or DNA concentration as determined by drug loading measurements) are incubated in cell culture medium at 37° C. Various amounts of Cathepsin B (0.5 to 1 µM) are added to the wells and similar concentrations of lysozyme (as irrelevant enzyme control) are added to determine specificity. At various intervals (e.g., 15 min, 30 min, 1 hr, 2 hrs, 6 hrs and 24 hrs), the lidded particles are separated by centrifugation and 200 µl of the supernatant is removed and replaced by fresh buffer. The collected buffer samples are subjected to HPLC measurements as detailed above to determine the concentration of the released drugs over time.

The above method of the present invention can also be scaled to make particles having a size of up to about 1000 microns.

Example 5

Fabrication of Nanoimprinted Particles

Fabrication of Thermally Imprinted Nanoparticles

Depending on the polymeric material used, both the thermal nanoimprint process and S-FIL™ process can be used to make drug delivery particles. In a particular embodiment, the thermal nanoimprint process is performed on a polymethylmethacrylate (PMMA) layer (300 nm thick, 950 kD in anisole) spun on a 4-inch silicon substrate. Prior to imprinting, the imprint template is treated with a self-assembled monolayer (SAM) of Dow-Corning release agent 20 to facilitate the separation of the template from the PMMA layer. The PMMA film is then heated above its glass transition temperature (105° C.) using a heater chuck under the wafer and the imprint template is pressed into the PMMA for 10 minutes using a micromanipulator with a built-in force sensor. Experiments are conducted to determine the appropriate pressure for an imprint depth of about 200 nm. The template is then lifted using the micromanipulator and separated from the wafer after the wafer temperature had reduced to 60° C. Finally, residual PMMA is removed using timed oxygen plasma cleaning and the PMMA nano-devices are released in water.

In an alternate embodiment, the thermal nanoimprint process is performed on poly(lactic-co-glycolic acid) (PLGA) polymer layer (300 nm thick) spun on a 4-inch silicon substrate. PLGA is an FDA approved, biocompatible and biodegradable polymer widely used for drug delivery, tissue engineering, surgical sutures. Although particles fabricated using PLGA releases drug purely by diffusion and degradation and is not disease-responsive, the process developed here allows for a novel fabrication method that provides highly monodisperse particles of precise size and shape along with a high drug loading efficiency. For spin coating, the polymer is first dissolved in dichloromethane and spun on the silicon wafer. The layer thickness is optimized by varying the spinning speed and the polymer concentration (i.e. viscosity).

Figure 6:
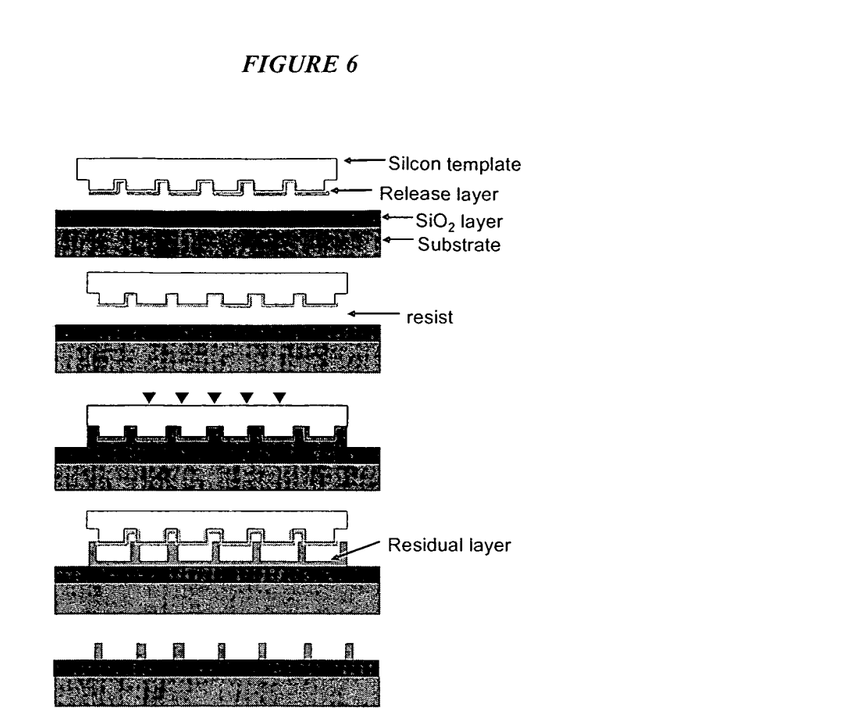
FIG. 6 is a schematic diagram of the fabrication process of solid nanoparticles of various sizes and shapes using thermal nanoimprinting: (6A) spin on release layer onto imprint template; (6B) spin on polymer; (6C) apply pressure and heat; (6D) after the template is separated from the wafer, (6E) after a timed oxygen plasma cleaning of monomer residual.
Figure 7:
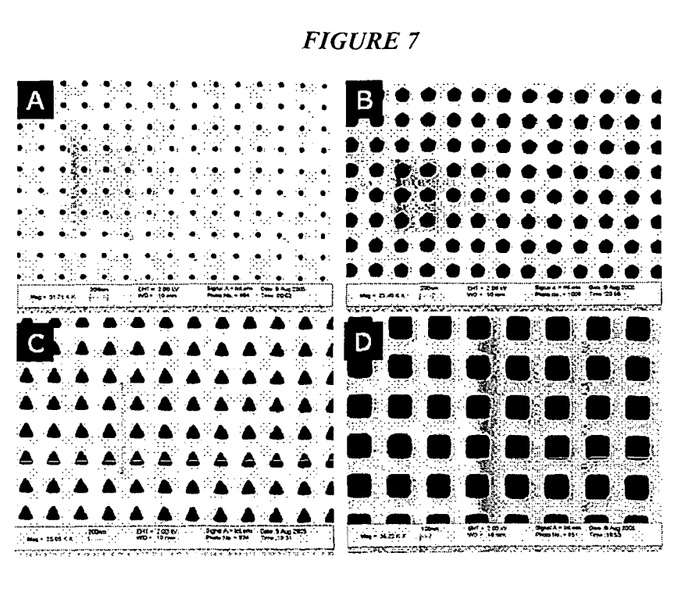
FIG. 7 shows SEM images of e-beam imprint template for nanofabricated solid particles.

FIG. 6 shows a schematic diagram of a procedure for nanoparticle fabrication using thermal nanoimprinting. Prior to imprinting, the imprint template is treated with a self-assembled monolayer (SAM) of Dow-corning release agent 20 to facilitate the separation of the template from the polymer layer. Next, the PLGA layer is spun onto the wafer and the polymeric film is heated above the glass transition temperature (50° C. for PLGA) using a heater chuck under the wafer. Subsequently, the imprint template is pressed into the PMMA for 10 min using a micromanipulator with a built-in force sensor. The template is then lifted using the micromanipulator and separated from the wafer after the wafer temperature had reduced to 40° C. Finally, residual PLGA is removed using timed oxygen plasma cleaning.

Fabrication of Nanoimprint Templates

To make a nanoparticle for use as a monodisperse drug carrier, a reusable nano-imprint template with various shapes was created using e-beam lithography and reactive ion etching. Four inch p-type <100> silicon test wafers were pre-cleaned with Pirhana. The wafers were then pre-baked (180° C., 30 s), spin coated with ZEP520 (3000 rpm for 60 sec.), and finally soft-baked (180° C., 30 sec.). Next the wafers were patterned using e-beam lithography (JEOL JBX-6000FS/E) with the following process parameters: EOS mode 7, 50 kV, 100 pA, exposure level/dose: 20 to −20. Between each step the wafers were developed with ZED n50 (15-30 sec.), rinsed with IPA (30 sec.), and dry etched using a Plasma Therm 790 Series Reactive ion etcher (gases: HBr, $Cl_2$, He) to etch the silicon surface below.

Fabrication of Disease-Responsive Nanoparticles Using S-FIL™

Figure 8:
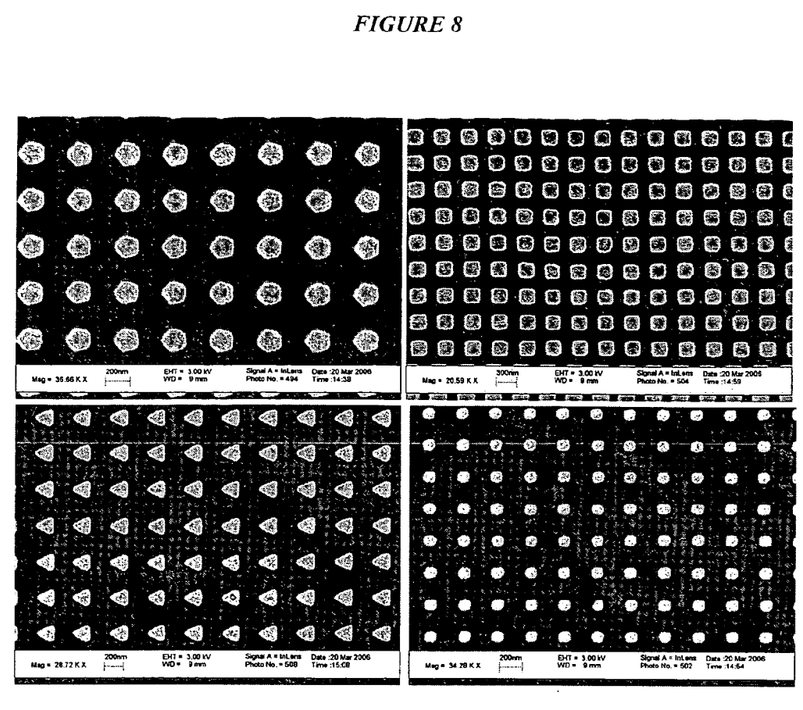
FIG. 8 shows SEM images imprinted PEGDA solid nanoparticles using the template from FIG. 7 and the S-FIL process. (8A, top left) 200 nm pentagons; (8B, top right) 200 nm squares; (8C, bottom left) 200 nm triangles; (8D, bottom right) 100 nm squares.

In a particular embodiment of the present invention, we have employed the S-FIL™ method using an IMPRIO100 S-FIL tool to directly imprint peptide-functionalized PEG membranes onto a silicon substrate. The step and flash process allows for high-throughput, wafer-scale patterning of the photolinkable polymer into drug delivery vehicles. To show that the peptide functionalized polymer membranes could be photopolymerized and imprinted using S-FIL, we imprinted the polymer using a standard template with nano-line array patterns. The step and flash process allows for high-throughput, wafer-scale patterning of the photo crosslinkable polymer into solid, drug loaded nano-carriers. In this process, the quartz template was treated with a release layer (Relmat) and loaded on the IMPRIO 100. Five microliters of the enzyme-responsive polymer was then dropped onto the wafer. Subsequently the template was pressed onto the wafer and then exposed to UV light and cured for 90 sec. The imprint force and time is optimized, and is in the range of 2-3 N and 1-2 minute, respectively. The template is then lifted by the S-FIL tool and separated from the wafer. A short, oxygen plasma cleaning is used to clean the residual polymer and separate the particles. The nanoimprinted particles are released similar to the process described supra using either diluted HF, mild basic solution, or DI water. FIG. 8 shows images of 100-200 nm particles fabricated according to the method of the invention. Particles on the order of 400 nm were also fabricated according to the method of the invention (data not shown). Atomic force microscopy was used to determine the height of the particles, which were determined to be approximately 200 nm high.

The number of lidded particles and particles that can be obtained from a single silicon wafer can be calculated. Using a 4" wafer, approximately $2.78 \times 10^9$ 50 µm×50 µm containers or particles can be fabricated if using a minimum spacing of 4 µm. For 300 nm×300 nm nanocontainers or particles, approximately $2.25 \times 10^{10}$ can be fabricated if using a minimum spacing of 300 nm. These values are similar to that obtained from approximate 10 to 100 mg of polymer micro- or nanocontainers or micro- or nanoparticles using emulsion processes. Therefore, a single wafer processing yields container or particle numbers equivalent to a medium scale particle synthesis using conventional bottom methods. Details of the calculations are provided in FIG. 9.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

All patents, patent applications, publications, products descriptions, and protocols, and references cited herein are incorporated by reference for all purposes, and specifically for a referenced method or procedure.

We claim:

1. A method for making a plurality of monodisperse, solid particles comprising:
   placing, on a silicon substrate, a patternable biodegradable polymer comprising a therapeutic agent, an imaging contrast agent, or both incorporated into a polymer matrix of the polymer;
   placing a release layer on an imprint template;
   imprinting the polymer by pressing the release layer and imprint template into the polymer, thereby forming a plurality of monodisperse, solid particles between 50 nm and 1000 nm in size corresponding to a plurality of particle-shaped portions of the imprint template and containing the therapeutic agent, an imaging contrast agent, or both, and also forming a residual polymer layer on the silicon substrate;
   removing the imprint template;
   oxygen plasma cleaning the plurality particles and residual polymer layer on the silicon substrate to remove the residual polymer layer; and
   releasing the plurality of particles.

2. The method of claim 1, further comprising forming the imprint template using e-beam lithography, reactive ion etching, or both.

3. The method of claim 1, wherein the polymer comprises a compound comprising, polyethylene glycol functionalized peptide, biodegradable photocrosslinkable polymers, biodegradable acrylate functionalized polymers, poly(D,L-lactide-co-glycolide), polylactic acid, polyglycolic acid, polycaprolactone, polyethylene glycol, or a combination thereof.

4. The method of claim 1, wherein imprinting comprises applying pressure and heat to the imprint template.

5. The method of claim 1, wherein the imaging contrast agent comprises an MRI imaging agent.

6. The method of claim 1, wherein the imaging contrast agent comprises a quantum dot or a gold nanoparticle.

7. The method of claim 1, wherein releasing the plurality of particles comprises releasing with water.

8. The method of claim 1, wherein placing the patternable biodegradable polymer on the silicon substrate comprises spin-coating.

9. The method of claim 1, wherein the imprint template is pressed into the polymer and removed from the polymer with a micromanipulator.

10. The method of claim 1, wherein the imprint has a depth of 200 nm.

11. The method of claim 1, wherein the monodisperse, solid particles are from 50 nm to 300 nm in size.

12. A method for making a plurality of monodisperse, solid particles comprising:
   placing, on a silicon substrate, a patternable biodegradable polymer comprising a therapeutic agent, an imaging contrast agent, or both incorporated into a polymer matrix of the polymer;
   placing a release layer on an imprint template;
   imprinting the polymer by pressing the release layer and imprint template into the polymer, thereby forming a plurality of monodisperse, solid particles between 50 nm and 1000 nm in size corresponding to a plurality of particle-shaped portion of the imprint template and containing the therapeutic agent, an imaging contrast agent, or both, and also forming a residual polymer layer on the silicon substrate;
   removing the imprint template;
   oxygen plasma cleaning the plurality particles and residual polymer layer on the silicon substrate to remove the residual polymer layer; and
   releasing the plurality of particles,
   wherein the biodegradable polymer is sensitive to a biomolecule, light, a magnetic field, ultrasound, pH or temperature, resulting in release the therapeutic agent.

13. The method of claim 12, further comprising forming the imprint template using e-beam lithography, reactive ion etching, or both.

14. The method of claim 12, wherein the polymer comprises a compound comprising, polyethylene glycol functionalized peptide, biodegradable photocrosslinkable polymers, biodegradable acrylate functionalized polymers, poly(D,L-lactide-co-glycolide), polylactic acid, polyglycolic acid, polycaprolactone, polyethylene glycol, or a combination thereof.

15. The method of claim 12, wherein imprinting comprises applying pressure and heat to the imprint template.

16. The method of claim 12, wherein the imaging contrast agent comprises an MRI imaging agent.

17. The method of claim 12, wherein the imaging contrast agent comprises a quantum dot or a gold nanoparticle.

18. The method of claim 12, wherein releasing the plurality of particles comprises releasing with water.

19. The method of claim 12, wherein placing the patternable biodegradable polymer on the silicon substrate comprises spin-coating.

20. The method of claim 12, wherein the imprint template is pressed into the polymer and removed from the polymer with a micromanipulator.

21. The method of claim 12, wherein the imprint has a depth of 200 nm.

22. The method of claim 12, wherein the monodisperse, solid particles are from 50 nm to 300 nm in size.

* * * * *